US00PP37250P2

(12) United States Plant Patent
Holtmaat

(10) Patent No.: US PP37,250 P2
(45) Date of Patent: Feb. 3, 2026

(54) ***RUDBECKIA* PLANT NAMED 'RUDLPIR734'**

(50) Latin Name: *Rudbeckia hirta*
Varietal Denomination: RUDLPIR734

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/232,300

(22) Filed: Jun. 9, 2025

(30) Foreign Application Priority Data

Oct. 30, 2024 (EA) ..... 20242572

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP32,454 P2 * 11/2020 Holtmaat ..... A01H 5/02
Plt./339

* cited by examiner

*Primary Examiner* — Susan Mccormick Ewoldt
(74) *Attorney, Agent, or Firm* — Penny J. Aguirre

(57) ABSTRACT

A new cultivar of *Rudbeckia* plant named 'RUDLPIR734' that is characterized by its compact plant habit, its single whorl of ray florets per inflorescence, its ray florets that are bi-colored with the upper portion yellow-orange and the lower half flushed greyed-purple, and its fast production time and flowers quickly after propagation.

2 Drawing Sheets

CROSS-REFERENCE TO A RELATED APPLICATION

This application claims priority to European Community Plant Variety Office (CPVO) Plant Breeder's Rights Application No. 2024/2572 filed on Oct. 30, 2024, under 35 U.S.C. 119(f), the entire contents of which is incorporated by reference herein. This application is co-pending with a U.S. Plant Patent Applications filed for plants derived from the same breeding program that are entitled *Rudbeckia* Plant Named *Rudbeckia* Plant Named 'RUDBBCH767' (U.S. Plant patent application Ser. No. 19/232,149, pending)*, *Rudbeckia* Plant Named 'RUDBSS851' (U.S. Plant patent application Ser. No. 19/232,228, pending)* and *Rudbeckia* Plant Named 'RUDBKST704' (U. S. Plant patent application Ser. No. 19/232,186, pending)*.

Botanical classification: *Rudbeckia hirta*
Variety denomination: 'RUDLPIR734'

BACKGROUND OF THE INVENTION

The present invention relates to a new and distinct cultivar of *Rudbeckia hirta* and will hereafter by referred to by its cultivar name, 'RUDLPIR734'. The new cultivar is an herbaceous perennial grown for use as a landscape plant.

'RUDLPIR734' was selected in June of 2021 by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in February of 2022. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDLPIR734' as a unique cultivar of *Rudbeckia*.

1. 'RUDLPIR734' exhibits a compact plant habit.
2. 'RUDLPIR734' exhibits a single whorl of ray florets per inflorescence.
3. 'RUDLPIR734' exhibits ray florets that are bi-colored with the upper portion yellow-orange and the lower half flushed greyed-purple.
4. 'RUDLPIR734' exhibits a fast production time and flowers quickly after propagation.

'RUDLPIR734' can be compared to the *Rudbeckia* cultivars 'RUDHT53' (U.S. Plant Pat. No. 30,727) and 'Rubsol' (U.S. Plant Pat. No. 32,454). 'RUDHT53' is similar to 'RUDLPIR734' in having inflorescences and a plant height that are similar in size. 'RUDHT53' differs from 'RUDLPIR734' in having ray floret colors that are yellow-orange, with more yellowish tips and a slower time to develop and flower after propagation. 'Rubsol' is similar to 'RUDLPIR734' in having inflorescences that are similar in size and foliage that is similar in color. 'Rubsol' differs from 'RUDLPIR734' in having ray florets with apices that are more tapered and praemorse in shape and in starting flowering a couple weeks later in the season.

'RUDLPIR734' can also be compared to the co-pending cultivars of *Rudbeckia*; 'RUDBBCH767', 'RUDBSS851', and 'RUDBKST704'. 'RUDBBCH767' differs from 'RUDLPIR734' in having only four whorls of ray florets that are golden yellow in color. 'RUDBSS851' differs from 'RUDLPIR734' in having a single row of ray florets that are bi-colored. 'RUDBKST704' differs from 'RUDLPIR734' in having a single row of ray florets that are yellow-orange with a lighter yellow-orange tip.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDLPIR734' as grown outdoors in a 17-cm container in Zuidwolde, The Netherlands.

The photograph in FIG. 1 is a side view of 'RUDLPIR734' in bloom.

Figure 1:
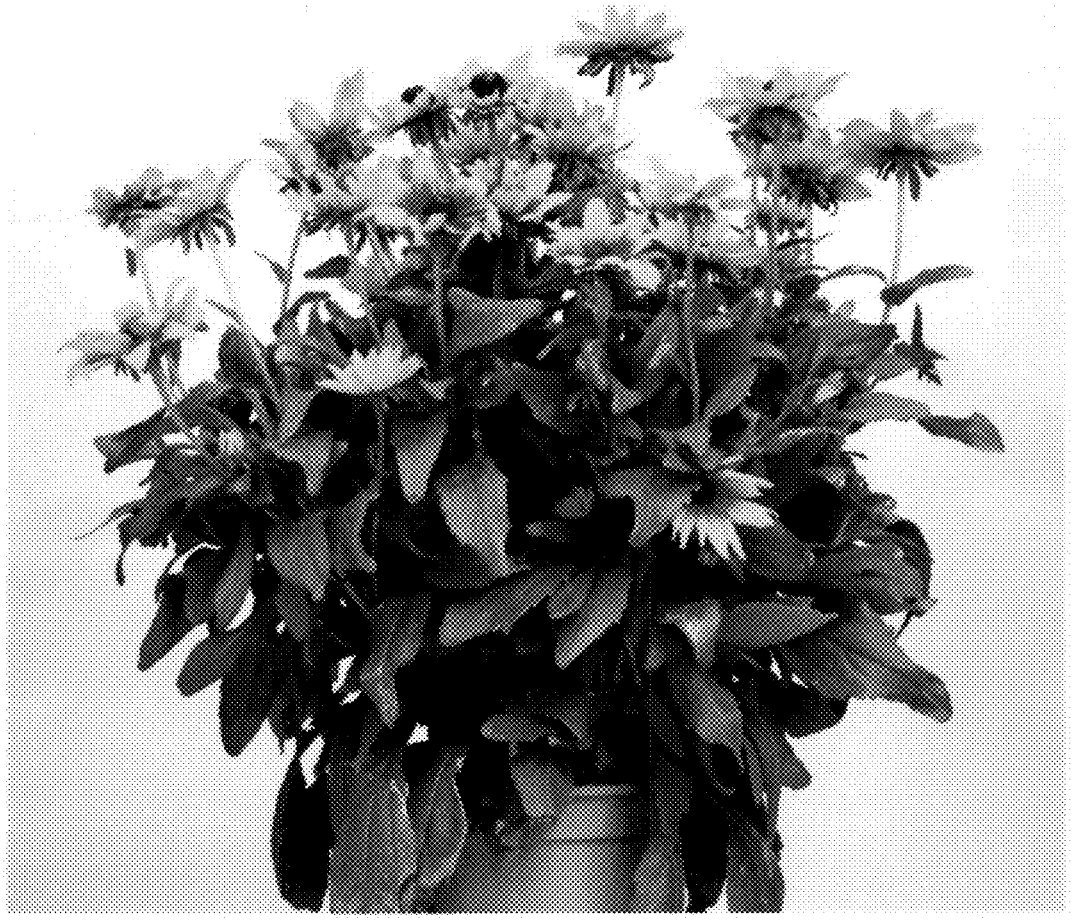
Figure 2:
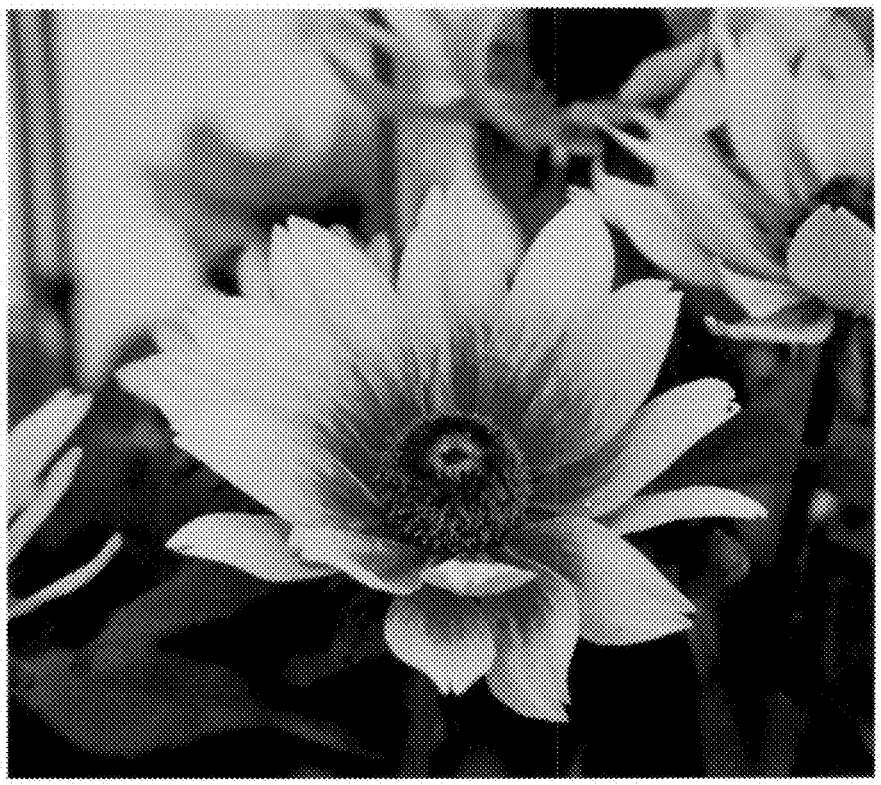

The photograph in FIG. 2 provides a close-up view of an inflorescence of 'RUDLPIR734'.

Figure 3:
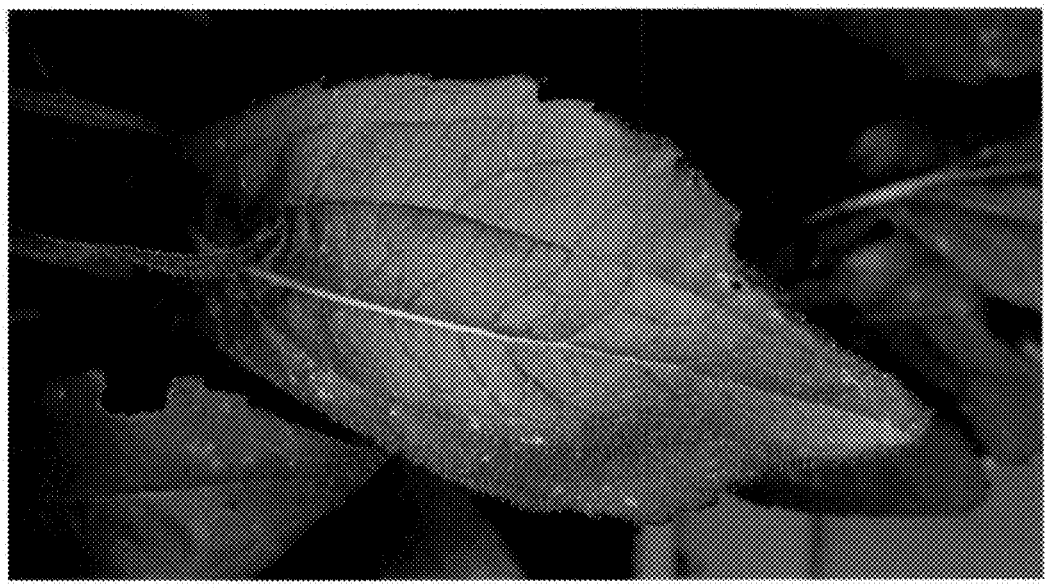

The photograph in FIG. 3 provides a close-up view of a leaf of 'RUDLPIR734'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDLPIR734' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with the 2015 (2019 reprint) Colour Chart of The Royal Horticultural Society, London, England, except where general color terms of ordinary dictionary significance are used.

General description:

*Blooming period*.—Early commencing; early June to July in The Netherlands.

*Plant type*.—Perennial.

*Plant habit*.—Upright, compact.

*Plant shape*.—Broad obovate to near globular.

*Height and spread*.—Average of 35 cm in height from soil level to top of foliar plane and 44 cm in height from soil level to top of floral plane, and 50 cm in diameter as a 3-month-old plant as grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Moderately to highly vigorous.

Stem description:

*Shape*.—Moderately angled, 5-sided.

*Stem color*.—Young and mature stems; 144A.

*Stem size*.—An average of 4 mm in diameter and an average of 19.5 cm in length.

*Stem surface*.—Moderately glossy and densely covered with strigose hairs an average of 1.5 mm in length and 156D in color.

*Stem number*.—Average of 7 main stems, 6 lateral branches per main stem.

*Internode length*.—An average of 3 cm in length.

*Stem aspect*.—Main stems; average of 35° to vertical, lateral branches; average of 15° to main stems.

*Branching*.—Freely branching from base with lateral stems.

Foliage description:

*Leaf shape*.—Narrow obovate.

*Leaf division*.—Simple.

*Leaf base*.—Long cuneate.

*Leaf apex*.—Rounded to bluntly acute.

*Leaf venation*.—Pinnate, color upper surface 147C, color lower surface 146B.

*Leaf margins*.—Coarsely shallowly crenate-serrate, coarsely slightly undulate.

*Leaf attachment*.—Petiolate.

*Leaf arrangement*.—Alternate.

*Leaf size*.—Average of 12.6 cm in length and 4.7 cm in width.

*Leaf color*.—Young upper surface; 143A, young lower surface; a blend of 143B and 144A, mature upper surface; 137B, mature lower surface; 146B.

*Leaf surface*.—Both surfaces slightly glossy and rough to the touch, densely pubescent with short strigose hairs; an average of 1.5 mm in length and 156D in color.

*Petioles*.—Average of 2 mm in length, flattened, average diameter at widest point 6 mm and at narrowest point 3 mm, upper surface color 144B to 144C, lower surface color 144B, both surfaces slightly glossy and densely covered with strigose hairs; an average of 1.5 mm in length and 156D in color.

Flower description:

*Type*.—Terminal capitulum, consisting of ray florets and disc florets.

*Capitulum number*.—10 per stem, up to 80 per plant.

*Lastingness of inflorescence*.—Average of 2 weeks, persistent.

*Capitulum size*.—Matures to about 4.5 cm in height and 8.6 cm in diameter, disc size is an average of 1.8 cm in diameter.

*Fragrance*.—None.

*Involucral bracts (phyllaries)*.—Cuneate base, bluntly acute apex, narrow oblong in shape, entire margins, average of 32 arranged in 3 rows, rotate, slightly to moderately curved downward in an angle of −40°, 2 cm in length and 4.5 mm in width, color; upper surface when fully open 137B, lower surface when fully open 146B, both surfaces slightly glossy, all surfaces including margins are densely covered with strigose hairs; an average of 1.5 mm in length and N155A in color.

*Receptacle*.—Ovate in shape, an average of 1.1 cm in height, 8 mm in diameter, color; 157B.

*Buds*.—Shape; flattened broadly ovate, immature ray florets pointed upward and slightly curled inwards, 2.4 cm in length, width; excluding and including involucral bracts 3.2 cm, color; immature ray florets 2A, upper side of immature involucral bracts 141B, under side of immature involucral bracts 138A, surfaces are matte and densely covered with strigose hairs, on immature ray florets 0.5 mm in length and NN155D in color, on involucral bracts 1 mm in length and NN155D in color.

*Peduncle*.—Strong, straight on top of main flowering stem, average of 8 cm in length and 3.5 mm in diameter, color; 143B, angled 143A, surface moderately glossy and moderately covered with short strigose hairs; an average of 1 mm in length and 156D in color.

*Ray florets*.—Average of 19, rotate around the disc in 1 row (whorl), narrow elliptic in shape, average of 4.1 cm in length and 1.5 cm in width, emarginate apex, cuneate base, entire margins, both surfaces are glabrous and moderately velvety, densely covered with very short hairs, 0.3 mm in length and 13B in color, held in an average angle of 20°, color; when opening upper surface 14A and 14B, lower half a blend of 17A and 21A, when opening lower surface 12A, when fully open upper surface 17A, lower half very strongly flushed 183B, when fully open lower surface 17B, tip 17C, veins 144B.

*Disc florets*.—Average of 800, 18 whorls arranged spirally on a conical receptacle, lower 92% fused into tube, tubular, upright, 7 mm in length and 3 mm in width, tubular, upper 8% free, free lobes have entire margins, apices of free lobes acute and curled backwards, both surfaces glabrous and very slightly glossy, color; when opening upper and lower surface 200B, lower half 158D, when fully open upper and lower surface 200A, lower half 157D, no spines, but a single bract is placed beside each disc floret; 1 per disc floret, flattened, an average of 5 mm in length and 1.5 mm in diameter, oblanceolate in shape, acute apex, narrowly cuneate base, color; apex N186C, mid-section N77D, narrowly margined N77B, base 155A, narrowly margined N77D, matte surface and moderately pubescent with hairs; an average of 0.2 mm in length, N186C in color.

Reproductive organs:

*Gynoecium*.—Pistil; 1, 7 mm in length, style; 4 mm in length, 155A in color, stigma; cleft, decurrent, 3 mm in diameter, 203A in color, ovary; 155A in color.

*Androecium*.—Stamens; 5, filaments; 1.5 mm in length, 155A in color, anther; narrow oblong in shape, 2.5 mm in length, 0.5 mm in width, 200A in color, pollen; moderate in quantity and 12A in color.

*Fruit/seed*.—None observed to date.

It is claimed:

1. A new and distinct cultivar of *Rudbeckia* plant named 'RUDLPIR734' substantially as herein illustrated and described.

* * * * *